(12) United States Patent
Chang et al.

(10) Patent No.: US 8,058,074 B2
(45) Date of Patent: Nov. 15, 2011

(54) 8-HYDROXYQUINOLINE ACETAMIDE COMPOUND, 8-HYDROXY QUINOLINE THIOAMIDE COMPOUND AND USE THEREOF

(75) Inventors: Suk Kyu Chang, Gwacheon-si (KR); Ki Cheol Song, Incheon (KR); Jun Soo Kim, Seoul (KR); Sang Mi Park, Seoul (KR); Sang Doo Ahn, Seoul (KR); Jae Young Sung, Seoul (KR)

(73) Assignees: Samsung Electronics Co., Ltd. (KR); Seoul National University Industry Foundation (KR); Chung-Ang University Industry-Academy Cooperation Foundation (KR)

( * ) Notice: Subject to any disclaimer, the term of this patent is extended or adjusted under 35 U.S.C. 154(b) by 1022 days.

(21) Appl. No.: 11/774,455

(22) Filed: Jul. 6, 2007

(65) Prior Publication Data
US 2008/0044913 A1 Feb. 21, 2008

(30) Foreign Application Priority Data
Aug. 17, 2006 (KR) ........................ 10-2006-0077550

(51) Int. Cl.
*G01N 33/20* (2006.01)
(52) U.S. Cl. .......................................... 436/81; 546/164
(58) Field of Classification Search ............... 436/81; 546/164
See application file for complete search history.

(56) References Cited

U.S. PATENT DOCUMENTS
2005/0227365 A1* 10/2005 Canary et al. ................... 436/81
2008/0182333 A1* 7/2008 Bentley et al. .................. 436/80

OTHER PUBLICATIONS

Chae, M.-Y.; Czarnik, A. W. J. Am. Chem. Soc. 1992, 114, 9704.
Yang, Y. K.; Yook, K. J.; Tae, J. J. Am. Chem. Soc. 2005, 127, 16760.
Zhang, G.; Zhang, D.; Yin, S.; Yang, X.; Shuai, Z.; Zhu, D. Chem. Commun. 2005, 2161.
Dujols, V.; Ford, F.; Czarnik, A. W. J. Am. Chem. Soc. 1997, 119, 7386.
Takahashi, Y.; Kasai, H.; Nakanishi, H.; Suzuki, T. M. Angew. Chem., Int. Ed. 2006, 45, 913.
Oehme, I.; Wolfbeis, O. S. Mikrochim. Acta 1997, 126, 177.
Bonfil, Y.; Brand, M.; Kirowa-Eisner, E. Anal. Chim. Acta 2002, 464, 99.
Kollmannsberger, M.; Rurack, K.; Resch-Genger, U; Rettig, W; Daub, J. Chem. Phys. Lett. 2000, 329, 363.
Rurack, K; Sczepan, M.; Spieles, M.; Resch-Genger, U.; Rettig, W. Chem. Phys. Lett. 2000, 320, 87.
Song, et al. Fluorgenic Hg2+-Selective Chemodosimeter Derived from 8-Hydroxyquinoline, Org. Lett., Jul. 7, 2006, vol. 8 No. 16, pp. 3413-3416.

* cited by examiner

*Primary Examiner* — Michael Marcheschi
*Assistant Examiner* — Jonathan Hurst
(74) *Attorney, Agent, or Firm* — Cantor Colburn LLP

(57) ABSTRACT

Disclosed are a novel 8-hydroxyquinoline acetamide compound, an 8-hydroxyquinoline thioamide and use thereof. More specifically, disclosed are a novel 8-hydroxyquinoline thioamide compound suitable for use as a selective chemodosimeter that shows considerably high detection sensitivity to mercury ions, an 8-hydroxyquinoline acetamide compound as an intermediate thereof, preparation thereof, and a chemodosimeter for mercury ion-selective detection, the chemodosimeter comprising the 8-hydroxyquinoline thioamide compound. The compounds as disclosed herein exhibit considerably effective fluorescence specificity of an off-on type, detect a micromole of mercury ions from chemical and biological aqueous systems, and allow 100% desulfurization within 5 minutes, thus being considerably useful in the chemical industry.

14 Claims, 10 Drawing Sheets

8-HYDROXYQUINOLINE ACETAMIDE COMPOUND, 8-HYDROXY QUINOLINE THIOAMIDE COMPOUND AND USE THEREOF

This non-provisional application claims priority to Korean Patent Application No. 10-2006-0077550, filed on Aug. 17, 2006, and all the benefits accruing therefrom under 35 U.S.C. §119(a) on, the content of which is herein incorporated by reference in its entirety.

BACKGROUND OF THE INVENTION

1. Field of the Invention

The present invention relates to a novel 8-hydroxyquinoline acetamide compound, an 8-hydroxyquinoline thioamide and use thereof. More specifically, the present invention relates to a novel 8-hydroxyquinoline thioamide compound suitable for use as a selective chemodosimeter that shows considerable high detection sensitivity to mercury ions, an 8-hydroxyquinoline acetamide compound as an intermediate thereof, preparation thereof, and mercury ion-selective detection using the same.

2. Description of the Related Art

As used herein, the term "chemodosimeter" refers to a detection system that detects metal cations as a detection target via a chemical reaction, i.e. stoichiometric reaction. There are some differences between the chemodosimeter and the chemical sensor. Firstly, the chemodosimeter must react stoichiometrically with the target metal, whereas the chemical sensor interacts with the target in a very selective or specific way. Secondly, expression of specific fluorescent properties is irreversible which results from the structural changes of the chemodosimeter through the chemical reaction. In other words, once the chemical change undergone, the chemodosimeter does not return to an initial state in the same reaction system. In contrast, as the chemical sensor emits fluorescence via binding with the metal cations (without chemical changes), the thus-bound cations can be eliminated with the use of a strong chelating agent such as EDTA. Therefore, the chemical sensor involves a reversible process.

Recently, a great deal of research has been conducted to develop chemodosimeters and chemical sensors for use in selective and efficient detection of chemically or biochemically important ionic materials. It has been known that the most desirable technique to develop sensors selective and sensitive for a specific material is the use of a well-known and efficient binding site coupled with a suitable signaling subunit. In particular, various fluorescent functional groups have been introduced as the signaling subunit. This is because fluorescent functional groups have high sensitivity and easy signal-convertibility.

Various selective fluorescent chemodosimeters have been reported to date. For example, fluorescent-sensitive properties selective for mercury ions involved in desulfurization was reported by (a) Chae, M.-Y.; Czarnik, A. W. J. Am. Chem. Soc. 1992, 114, 9704. (b) Yang, Y. K.; Yook, K. J.; Tae, J. J. Am. Chem. Soc. 2005, 127, 16760. (c) Zhang, G.; Zhang, D.; Yin, S.; Yang, X.; Shuai, Z.; Zhu, D. Chem. Commun. 2005, 2161. In particular, Chae et. al., suggested a 9-[(methyl-amino) thiocarbonyl]anthracene compound serving as a chemodosimeter that expresses changes in the fluorescence emission behavior which results from desulfurization by mercury and silver ions. However, there remain problems in that the compound is selective for both mercury ions and silver ions and incomplete desulfurization (e.g. 87%) is carried out after 10 min.

Furthermore, a selective fluorescent variation for copper ions ($Cu^{2+}$) was reported by Dujols, V.; Ford, F.; Czarnik, A. W. J. Am. Chem. Soc. 1997, 119, 7386. Optically electrochemically sensitive properties for heavy metals such as mercury ($Hg^{2+}$), lead ($Pb^{2+}$) and cadmium ($Cd^{2+}$) were reported by (a) Takahashi, Y.; Kasai, H.; Nakanishi, H.; Suzuki, T. M. Angew. Chem., Int. Ed. 2006, 45, 913, (b) Oehme, I.; Wolfbeis, O, S. Mikrochim. Acta 1997, 126, 177, (c) Bonfil, Y.; Brand, M.; Kirowa-Eisner, E. Anal. Chim. Acta 2002, 464, 99, etc. A selective fluorescent sensitive properties for alkali metal ions and alkaline earth metal ions was reported by (a) Kollmannsberger, M.; Rurack, K.; Resch-Genger, U; Rettig, W; Daub, J. Chem. Phys. Lett. 2000, 329, 363, (b) Rurack, K; Sczepan, M.; Spieles, M.; Resch-Genger, U.; Rettig, W. Chem. Phys. Lett. 2000, 320, 87, etc.

Meanwhile, toxicity of mercury ions was well-known in environmental fields, and continuous development for various sensors capable of sensitively and selectively detecting mercury ions under various conditions have been thus made in the fields. The sensors necessarily exhibit significant variation in spectroscopic properties in response to binding to mercury ions. The use of fluorescent properties for the sensors is based on ease of quantitative analysis or signal conversion.

However, the fore-mentioned methods for detecting metal ions, in particular, chemodosimeters exhibiting a selective fluorescent sensitivity for mercury ions involved in desulfurization have some problems in that it takes a long time to increase fluorescence intensity in response to desulfurization or has low detection sensitivity because of an insufficient increase in the level of fluorescence intensity, when compared to the value prior to desulfurization. Furthermore, there is a limitation on exclusive detection of mercury ions because of undesired detection of other ions (e.g. silver ions) in addition to mercury ions.

BRIEF SUMMARY OF THE INVENTION

Exemplary embodiments of the present invention have been made in view of the problems of the prior art, and in one embodiment, a novel 8-hydroxyquinoline thioamide compound suitable for use as mercury ions-selective chemodosimeter that has considerable high detection sensitivity to mercury ions, an 8-hydroxyquinoline acetamide compound as an intermediate thereof and preparation thereof are provided.

In another embodiment, a chemodosimeter for selective detection of mercury ions which comprises an 8-hydroxyquinoline thioamide compound represented by Formula 3 and a method for selectively detecting mercury ions using the chemodosimeter are provided.

In accordance with one embodiment, there is provided an 8-hydroxyquinoline acetamide compound represented by Formula 2 below:

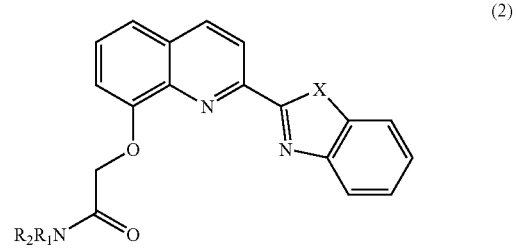

(2)

wherein X is S, O or NH; and $R_1$ and $R_2$ are each independently $C_{1-4}$ linear or branched alkyl.

Preferably, the compound of Formula 2 may be 2-(2-(benzo[d]thiazol-2-yl)quinoline-8-yloxy)-N,N-diethylacetamide, 2-(2-(benzo[d]thiazol-2-yl)quinoline-8-yloxy)-N,N-dimethylacetamide, 2-(2-(benzo[d]thiazol-2-yl)quinoline-8-yloxy)-N,N-dipropylacetamide, or 2-(2-(benzo[d]thiazol-2-yl)quinoline-8-yloxy)-N,N-dibutylacetamide.

In accordance with another embodiment, there is provided an 8-hydroxyquinoline thioamide compound represented by Formula 3 below:

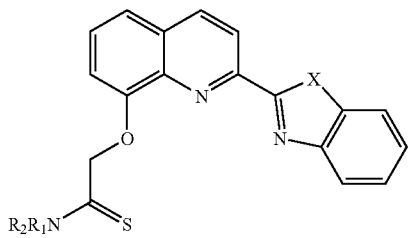

(3)

wherein X is S, O or NH; and $R_1$ and $R_2$ are each independently $C_{1-4}$ linear or branched alkyl.

Preferably, the compound of Formula 3 may be 2-(2-(benzo[d]thiazol-2-yl)quinoline-8-yloxy)-N,N-diethyl-ethanethioamide, 2-(2-(benzo[d]thiazol-2-yl)quinoline-8-yloxy)-N,N-dimethylethanethioamide, 2-(2-(benzo[d]thiazol-2-yl)quinoline-8-yloxy)-N,N-dipropylethanethioamide, or 2-(2-(benzo[d]thiazol-2-yl)quinoline-8-yloxy)-N,N-dibutylethanethioamide.

In accordance with another embodiment, there is provided a method for preparing an 8-hydroxyquinoline acetamide compound by reacting an 8-hydroxyquinoline compound represented by the following Formula 1 with 2-chloro-N,N-diethylacetamide, potassium carbonate and potassium iodide in an organic solvent under an inlet gas atmosphere.

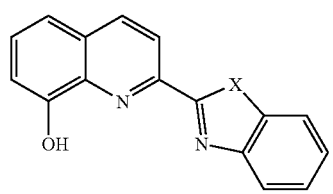

(1)

wherein X is S, O or NH.

Preferably, the molar ratio of the 8-hydroxyquinoline compound of Formula 1, 2-chloro-N,N-diethylacetamide, potassium carbonate and potassium iodide may be 1:1.2-2.0:1.0-2.0:0.05-0.2

The organic solvent may be tetrahydrofuran (THF).

In accordance with another embodiment, there is provided a method for preparing an 8-hydroxyquinoline thioamide compound represented by the following Formula 3 by reacting the 8-hydroxyquinoline acetamide compound of Formula 2 with a Lawesson's reagent in an organic solvent.

In preparation of the 8-hydroxyquinoline thioamide compound of Formula 3, the molar ratio of the 8-hydroxyquinoline acetamide compound to the Lawesson's reagent may be preferably 1:1.0-1.5. The organic solvent may be preferably toluene.

In accordance with another embodiment, there is provided a method for synthesizing an 8-hydroxyquinoline thioamide compound with selectivity for mercury ions as depicted in the following Reaction Scheme 1, the method comprising:

1) reacting an 8-hydroxyquinoline compound 1 represented by the following Formula 1 with 2-chloro-N,N-diethylacetamide, potassium carbonate and potassium iodide in an organic solvent under an inlet gas atmosphere to prepare an 8-hydroxyquinoline acetamide compound represented by Formula 2; and 2) reacting the 8-hydroxyquinoline acetamide compound with Lawesson's reagent in an organic solvent to prepare an 8-hydroxyquinoline thioamide compound represented by the following Formula 3.

Reaction Scheme 1

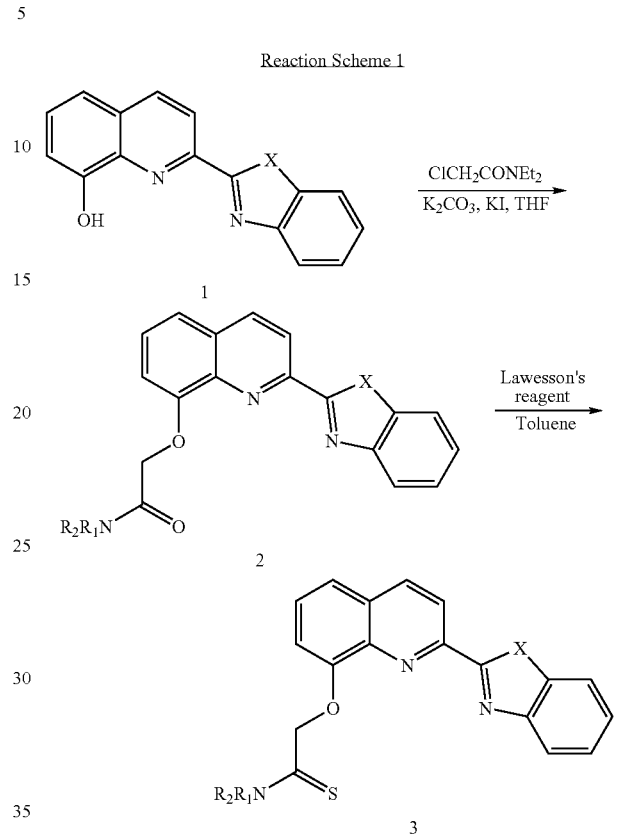

wherein X is S, O or NH; and $R_1$ and $R_2$ are each independently $C_{1-4}$ linear or branched alkyl.

In accordance with another embodiment, there is provided a chemodosimeter for mercury ion-selective detection, the chemodosimeter comprising the 8-hydroxyquinoline thioamide compound of Formula 3.

In accordance with yet another embodiment, there is provided a method for selectively detecting mercury ions, the method comprising:

dissolving the 8-hydroxyquinoline thioamide compound of Formula 3 in water, acetonitrile, or a mixed solvent of water and acetonitrile;

adding a desired reagent to the solution; and detecting mercury ions by analyzing a fluorescence spectrum involved in desulfurization of mercury ions contained in the reagent with the 8-hydroxyquinoline thioamide compound, as depicted in the following Reaction Scheme 2:

Reaction Scheme 2

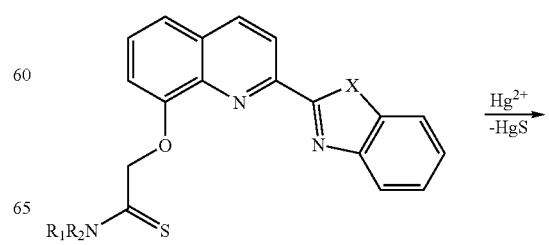

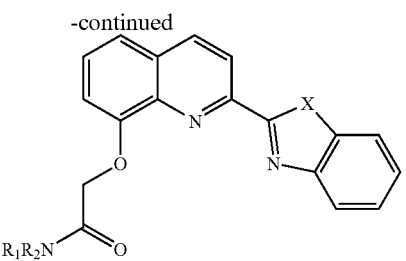

wherein X is S, O or NH; and $R_1$ and $R_2$ are each independently $C_{1-4}$ linear or branched alkyl.

Preferably, water and acetonitrile of the mixed solvent may be used in a ratio of 1:99-99:1.

The minimum detectable concentration of mercury ions may be $5.4 \times 10^{-7}$ M.

BRIEF DESCRIPTION OF THE DRAWINGS

The above and other features and advantages of the present invention will be more clearly understood from the following detailed description taken in conjunction with the accompanying drawings, in which.

DETAILED DESCRIPTION OF THE PREFERRED EMBODIMENTS

Figure 1:
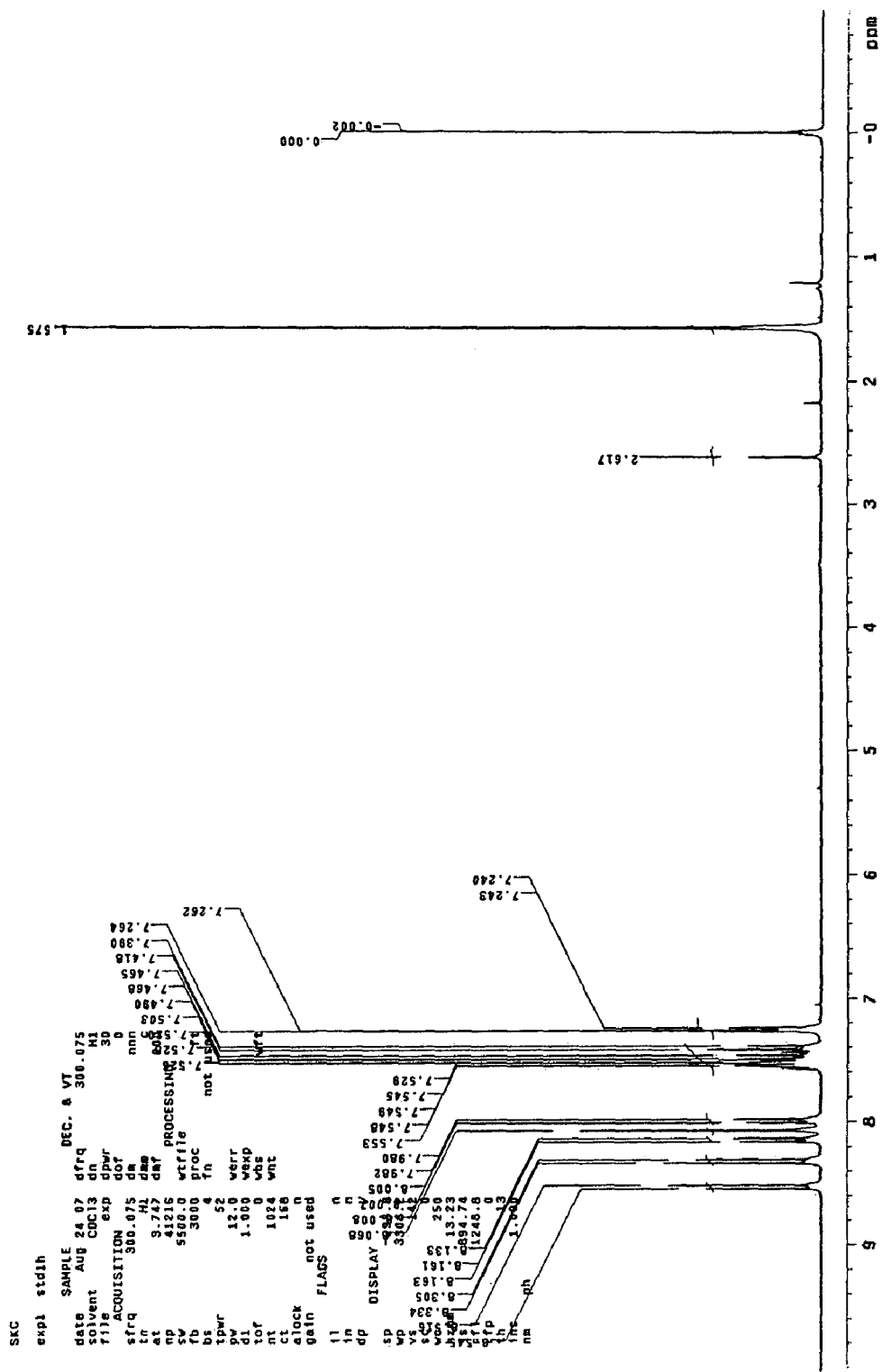
FIG. 1 is a $^1$H-NMR spectrum of an 8-hydroxyquinoline compound represented by Formula 1 according to the present invention.

The present invention will now be described in greater detail with reference to the accompanying drawings.

In one aspect, the present invention is directed to a novel 8-hydroxyquinoline thioamide compound of Formula 3, which has a structure where benzo[d]thiazol and N,N-diethylethanethioamide moieties are introduced into an 8-hydroxyquinoline skeleton, imparting selective fluorescence enhancement for highly toxic mercury ions to the compound for easy and selective detection of mercury, and a novel 8-hydroxyquinoline acetamide compound represented by Formula 2 as an intermediate thereof.

A more detailed explanation of the 8-hydroxyquinoline acetamide compound represented by the following Formula 2 will be given below:

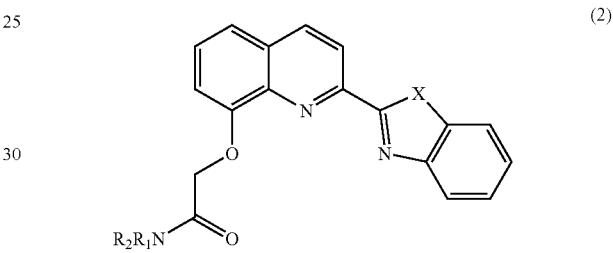

wherein X is S, O or NH; and $R_1$ and $R_2$ are each independently $C_{1-4}$ linear or branched alkyl.

The 8-hydroxyquinoline acetamide compound of Formula 2, which is an intermediate of a novel 8-hydroxyquinoline thioamide compound represented by Formula 3, is prepared from a well-known 8-hydroxyquinoline compound represented by Formula 1 as a starting material. A detailed explanation for preparation thereof will be given in the related section.

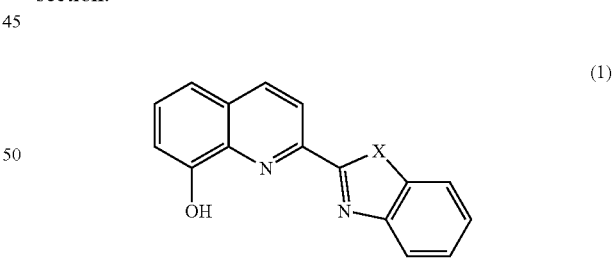

wherein X is S, O or NH.

Specific examples of the compound of Formula 2 include 2-(2-(benzo[d]thiazol-2-yl)quinoline-8-yloxy)-N,N-diethylacetamide, 2-(2-(benzo[d]thiazol-2-yl)quinoline-8-yloxy)-N,N-dimethylacetamide, 2-(2-(benzo[d]thiazol-2-yl)quinoline-8-yloxy)-N,N-dipropylacetamide, 2-(2-(benzo[d]thiazol-2-yl)quinoline-8-yloxy)-N,N-dibutylacetamide and mixtures thereof.

The compound of Formula 2 is considered significant in that it is an intermediate of the compound of Formula 3 which actually serves as a chemodosimeter, but is stable and is restorable from the compound of Formula 3 via desulfurization caused by reaction of the compound of Formula 3 with mercury ions, as depicted in the following Reaction Scheme 1.

Then, a more detailed explanation of the 8-hydroxyquinoline thioamide compound represented by Formula 3 will be given below:

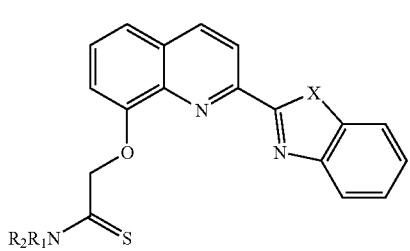
(3)

wherein X is S, O or NH; and $R_1$ and $R_2$ are each independently $C_{1-4}$ linear or branched alkyl.

The 8-hydroxyquinoline thioamide compound of Formula 3 is a novel compound capable of selectively detecting mercury ions only. The compound of Formula 3 can be prepared from the 8-hydroxyquinoline acetamide compound of Formula 2, but is not particularly limited to this compound.

The 8-hydroxyquinoline thioamide compound of Formula 3 has a structure where benzo[d]thiazol and N,N-diethylethanethioamide moieties are introduced into an 8-hydroxyquinoline skeleton, allowing selective fluorescence enhancement for mercury ions which are of considerable importance in environmental fields and are severely toxic for the purpose of easily detecting the mercury ions exclusively.

Specific examples of the compound of Formula 3 include 2-(2-(benzo[d]thiazol-2-yl)quinoline-8-yloxy)-N,N-diethylethanethioamide, 2-(2-(benzo[d]thiazol-2-yl)quinoline-8-yloxy)-N,N-dimethylethanethioamide, 2-(2-(benzo[d]thiazol-2-yl)quinoline-8-yloxy)-N,N-dipropylethanethioamide and 2-(2-(benzo[d]thiazol-2-yl)quinoline-8-yloxy)-N,N-dibutylethanethioamide and mixtures thereof.

The 8-hydroxyquinoline thioamide compound of Formula 3 is used as a chemodosimeter for selectively detecting mercury ions. The detection method using the compound 3 will be explained as follows.

First, the 8-hydroxyquinoline thioamide compound of Formula 3 is dissolved in water, acetonitrile or a mixture thereof as a solvent. In a case where a mixture of water and acetonitrile is used as a solvent, a mixed ratio of water and acetonitrile is not particularly limited. A concentration of the 8-hydroxyquinoline thioamide compound in the solvent is preferably adjusted to $1.0 \times 10^{-6}$ M to $2 \times 10^{-5}$ M.

The use of water, acetonitrile or a mixture thereof as a solvent is necessary for specific detection of mercury ions. The use of other solvents instead of these solvents causes an increase in reactivity of the 8-hydroxyquinoline thioamide compound to other metal ions as well as mercury ions, thus making it difficult to use the compound as a selective chemodosimeter.

Then, a desired reagent is added to the 8-hydroxyquinoline thioamide compound solution. The reagent may be body fluids for measurement of the contamination level of purified water or sewage, or confirmatory test for mercury poisoning in the human body, but is not particularly limited thereto.

Mercury ions can be detected by measuring a fluorescence spectrum which results from desulfurization of mercury ions in the reagent with the 8-hydroxyquinoline thioamide compound, as depicted in the following Reaction scheme 2. In this case, a minimum detectable concentration of mercury ions is $5.4 \times 10^{-7}$ M. Accordingly, the chemodosimeter according to the present invention is different from general chemodosimeters for detection of mercury ions in that it can detect mercury ions even although an extremely small amount of the mercury ions are contained in the reagent.

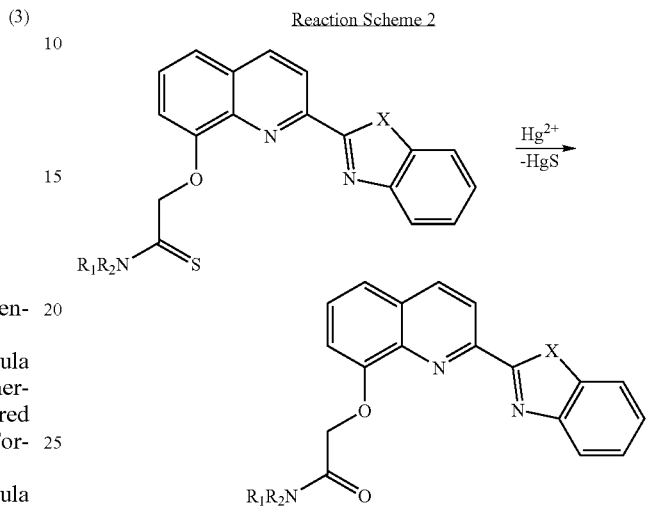
Reaction Scheme 2 wherein X is S, O or NH; and $R_1$ and $R_2$ are each independently $C_{1-4}$ linear or branched alkyl.

Figure 6:
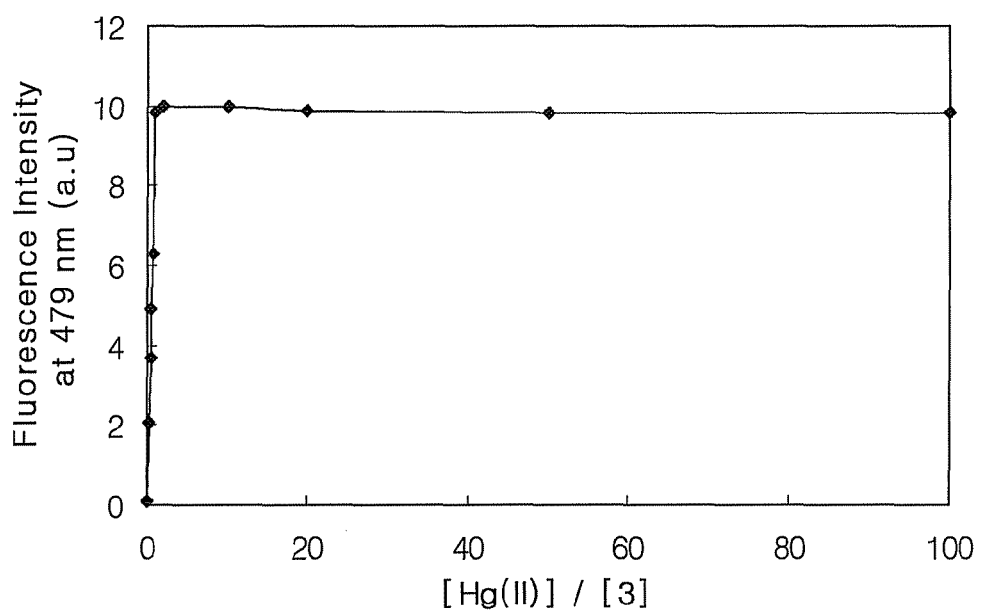
FIG. 6 is a fluorescence spectrum illustrating an 8-hydroxyquinoline thioamide compound of Formula 3 of the present invention as a function of a mercury ion concentration.
Figure 7:
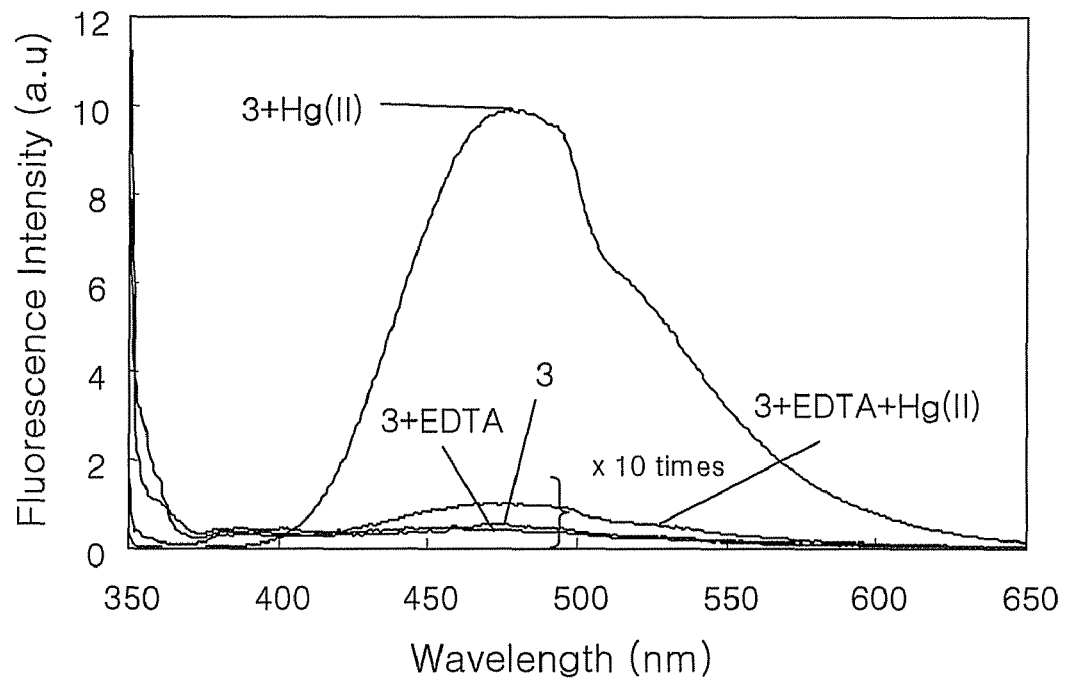
FIG. 7 is a fluorescence spectrum illustrating an 8-hydroxyquinoline thioamide compound of Formula 3 of the present invention according to mercury ions and EDTA.
Figure 8:
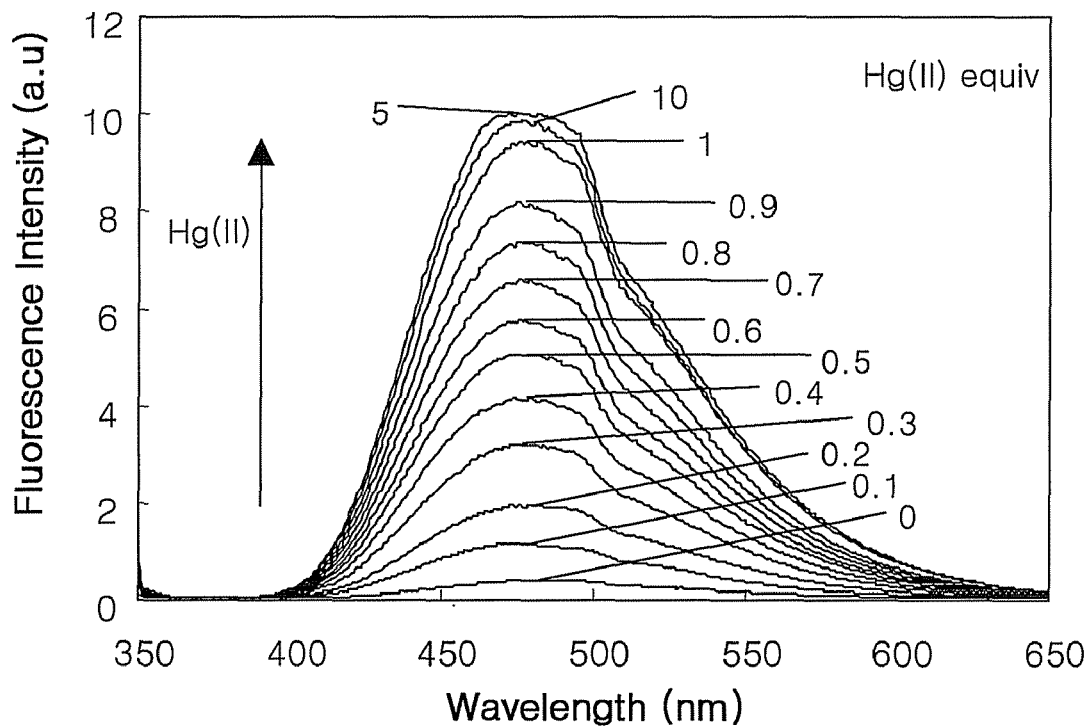
FIG. 8 is a fluorescence spectrum illustrating sensitivity of an 8-hydroxyquinoline thioamide compound of Formula 3 of the present invention for mercury ions in a system containing a great amount of physiologically important metal ions as a function of a mercury ion concentration.
Figure 9A:
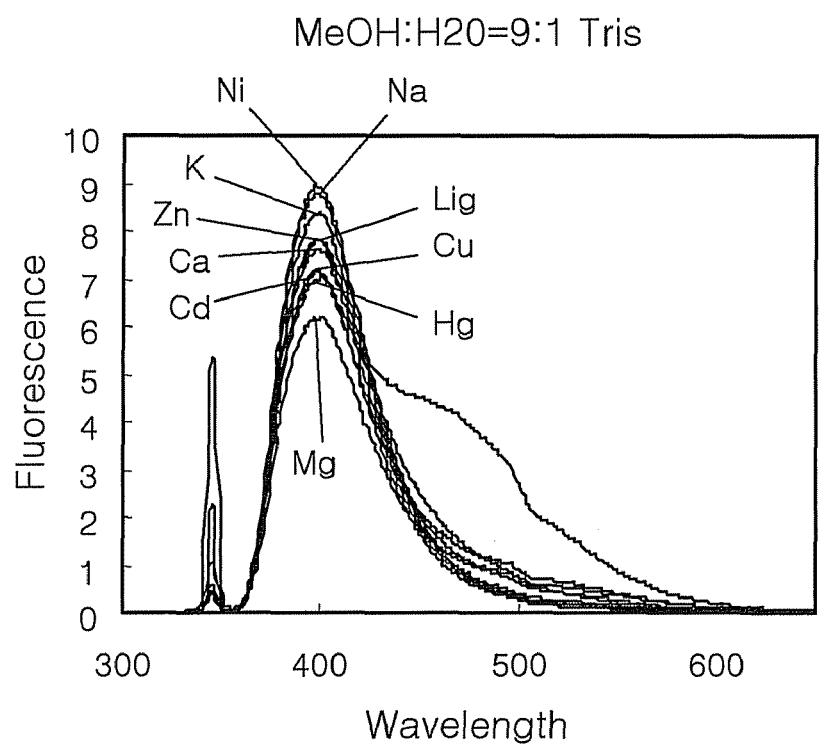
FIG. 9a is a fluorescence spectrum illustrating a detection result of metal ions under a Tris buffer solution after dissolving an 8-hydroxyquinoline thioamide compound of Formula 3 of the present invention in a mixed solvent of methanol and water (9:1, v/v)
Figure 9B:
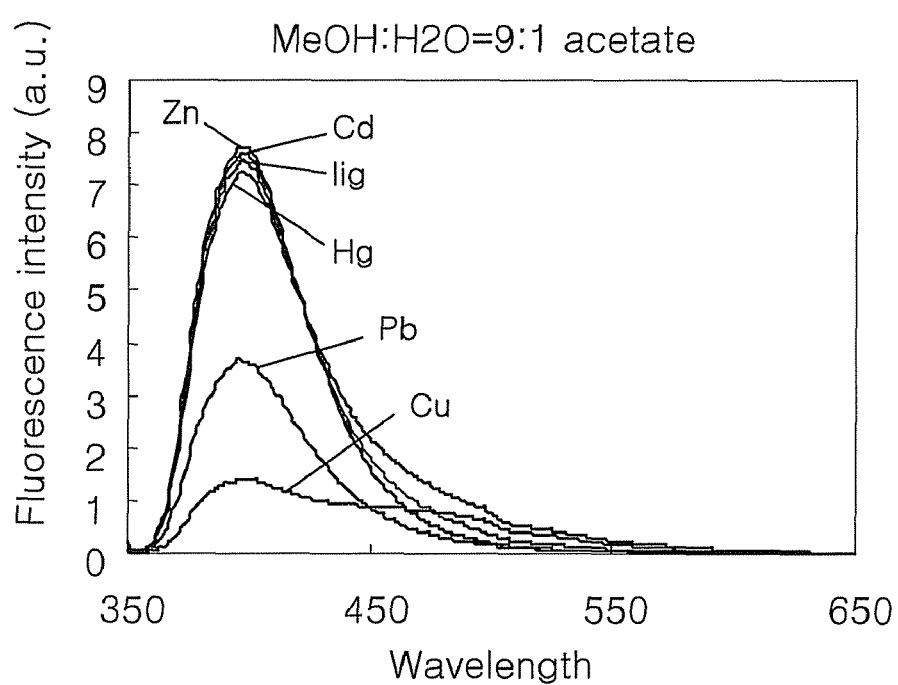
FIG. 9b is a fluorescence spectrum illustrating a detection result of metal ions under an acetate buffer solution.
Figure 10A:
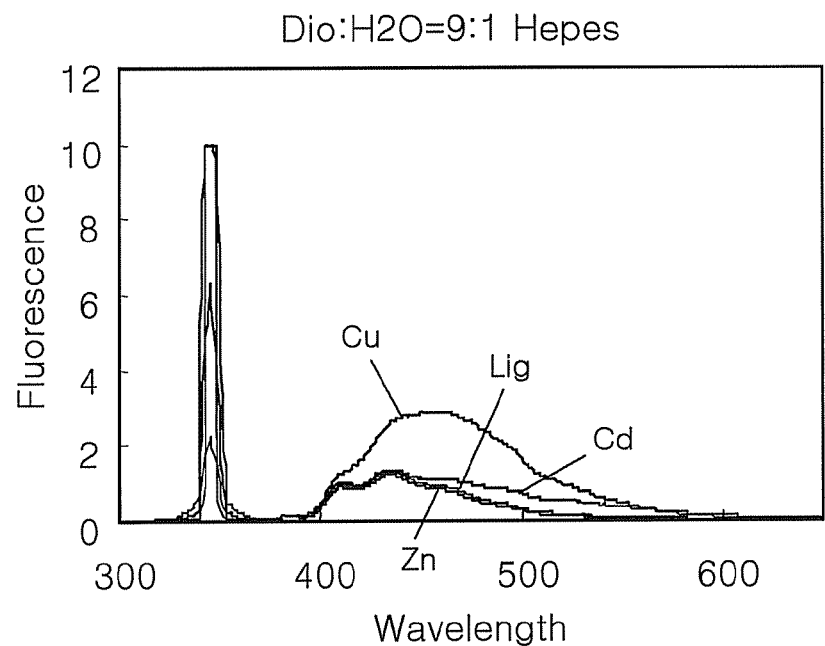
FIG. 10a is a fluorescence spectrum illustrating a detection result of metal ions under a Hepes buffer solution after dissolving an 8-hydroxyquinoline thioamide compound of Formula 3 of the present invention in a mixed solvent of dioxane and water (9:1, v/v)
Figure 10B:
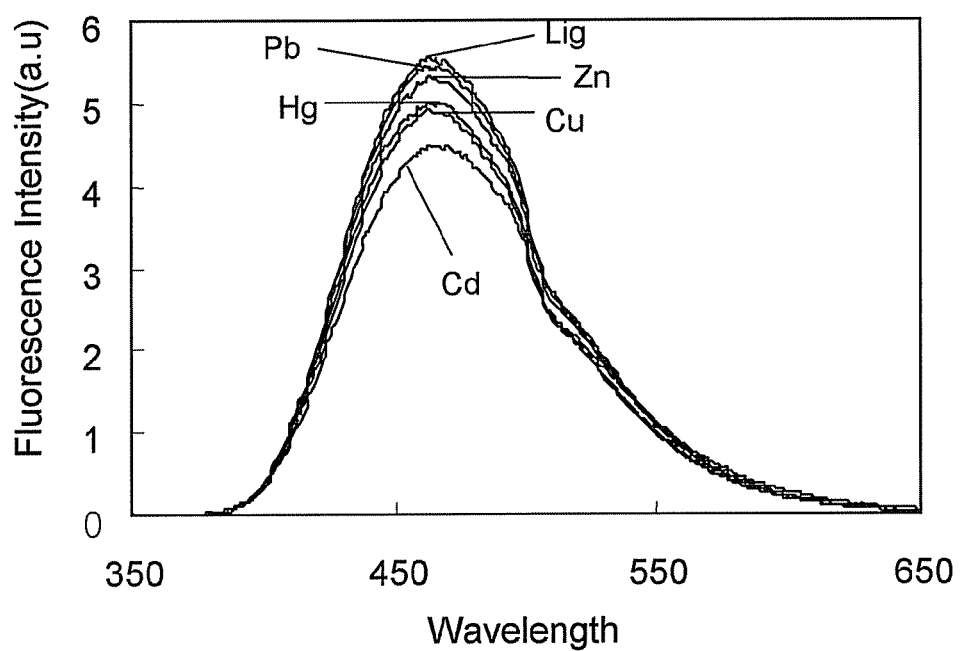
FIG. 10b is a fluorescence spectrum illustrating a detection result of metal ions under an acetate buffer solution.

The reason for the selective fluorescence enhancement of the compound of Formula 3 is that a thioamide group of the compound 3 is converted to an amide group via a chemical reaction of the compound 3 with mercury ions. The conversion of the compound of Formula 3 into the compound of Formula 2, as depicted in Reaction Scheme 2, can be confirmed from the test results shown in FIGS. 6 to 8.

The reaction is carried out by hydrolysis of a thioamide group into an amide group. In particular, the hydrolysis is known to be facilitated by some metal ions acting as catalysts. In this case, sulfur atoms removed by the hydrolysis are reacted with metal ions to form metal sulfide. The present invention is designed such that mercury ions only act as a specific catalyst rather than other metal ions. In addition, the present invention suggests optimal conditions for fluorescence signaling of the compound to mercury ions via systematic experiments in accordance with various reaction conditions.

Mercury analysis according to the present invention can be utilized in applications including: measurement of the degree of mercury contamination in drinking water (e.g., public water and groundwater) according to drinking water criterion; measurement of the concentration of mercury in high-concentration contaminants-containing water including industrial water or industrial sewage; and measurement of the degree of mercury contamination in foods including beverages, fish or shellfish.

Subsequently, a method for preparing the 8-hydroxyquinoline acetamide compound of Formula 2 will be mentioned in detail.

First, a more detailed explanation of preparation of an 8-hydroxyquinoline compound represented by the following Formula 1, which is a starting material of the 8-hydrox yquinoline acetamide compound of Formula 2, will be given below:

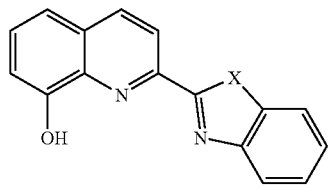
(1)

wherein X is S, O or NH.

The 8-hydroxyquinoline compound of Formula 1 is synthesized by reacting 8-hydroxyquinoline-2-carboxylic acid with 2-aminothiophenol and phosphorus trichloride ($PCl_3$) in toluene, as depicted in the following Reaction 3. 2-Aminothiophenol is used to prepare a compound where "X" in the Formula 1 is sulfur (S). To prepare a compound where "X" in the Formula 1 is O or NH, another suitable reagent may be used. More specifically, when X is oxygen (O), 8-hydroxyquinoline-2-carboxylic acid is reacted with 2-aminophenol and 8-hydroxyquinoline-2-carboxylic acid in polyphosphoric acid as a solvent. When X is NH, 8-hydroxyquinoline-2-carboxylic acid is reacted with manganese (III) acetate ($Mn(OAc)_3$) 1,2-diaminobenzene and 8-hydroxyquinoline-2-carboxaldehyde in acetic acid.

Reaction Scheme 3

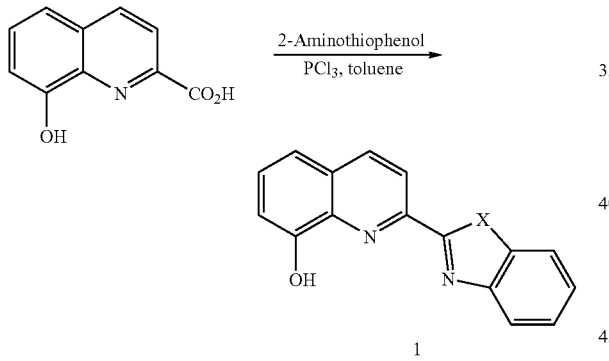

1

An 8-hydroxyquinoline acetamide compound of Formula 2 is prepared by reacting the 8-hydroxyquinoline compound of Formula 1, 2-chloro-N,N-diethyl acetamide, potassium carbonate and potassium iodide in an organic solvent under an inlet gas atmosphere.

Preferably, the molar ratio of the 8-hydroxyquinoline compound of Formula 1, 2-chloro-N,N-diethyl acetamide, potassium carbonate and potassium iodide is 1:1.2-2.0:1.0-2.0: 0.05-0.2.

Tetrahydrofuran (THF) may be used as the organic solvent.

First, a method for preparing an 8-hydroxyquinoline thioamide compound of Formula 3 will be mentioned in detail below:

In one aspect, the present invention is directed to a method for preparing an 8-hydroxyquinoline thioamide compound represented by Formula 3 by reacting the 8-hydroxyquinoline acetamide compound of Formula 2 with a Lawesson's reagent in an organic solvent.

In preparation of the 8-hydroxyquinoline thioamide compound of Formula 3, the molar ratio of the 8-hydroxyquinoline acetamide compound of Formula 2 to the Lawesson agent may be preferably 1:1.0-1.5, more Preferably, 1:1. The organic solvent may be preferably toluene.

In summary, the method for synthesizing an 8-hydroxyquinoline thioamide compound of Formula 3 depicted in the following Reaction Scheme 1 comprising the steps:

1) reacting an 8-hydroxyquinoline compound 1 represented by the following Formula 1, 2-chloro-N,N-diethyl acetamide, potassium carbonate and potassium iodide in an organic solvent under an inlet gas atmosphere to prepare an 8-hydroxyquinoline acetamide compound represented by Formula 2; and 2) reacting the 8-hydroxyquinoline acetamide compound of Formula 2 with a Lawesson's reagent in an organic solvent to prepare an 8-hydroxyquinoline thioamide compound represented by Formula 3.

Reaction Scheme 1

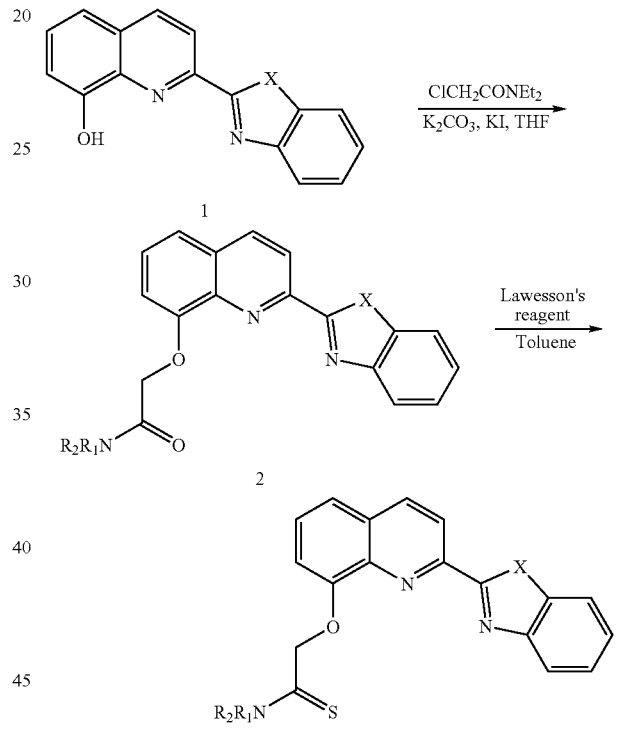

wherein X is S, Q or NH; and $R_1$ and $R_2$ are each independently $C_{1-4}$ linear or branched alkyl.

By introducing hydroxyquinoline as a well-known binding site, benzo[d]thiazol and N,N-diethylethanethioamide serving as both a signaling site and an additional binding site into the 8-hydroxyquinoline thioamide compound of Formula 3 according to the present invention, selectivity for mercury ions is imparted to the compound. Accordingly, the compound can be used as a selective chemodosimeter for mercury ions.

In addition, the compound of Formula 3 of the present invention can show effective fluorescence specificity of an off-on type and detect a micromole of mercury ions from chemical and biological aqueous systems, and allows 100% desulfurization within 5 minutes, thus realizing superior detection sensitivity and reduced detection time, as compared to conventional chemodosimeters for detection of mercury ions.

Hereinafter, the present invention will be explained in more detail with reference to the following examples. However, these examples are given for the purpose of illustration and are not to be construed as limiting the scope of the invention.

EXAMPLES

Synthesis Example

Synthesis of 2-(benzo[d]thiazol-2-yl)quinolin-8-ol

To introduce a benzo[d]thiazol group into an 8-hydroxyquinoline compound, 2-aminothiophenol (123 mg, 1.1 mmol) and 8-hydroxyquinoline-2-carboxylic acid (189 mg, 2 mmol) were dissolved in dry toluene (30 ml) with blown nitrogen to prevent oxidation which is caused by oxygen in air. The solution was heated to 40° C. and phosphrous trichloride (0.1 ml, 1.1 mmol) was slowly added thereto. Then, the reaction solution was heated at 100° C. for 24 hours and allowed to cool. The reaction mixture was extracted with a 20% aqueous sodium carbonate solution, distilled water and dichloromethane, dried and recrystallized with dichloromethane and hexane to yield 2-(benzo[d]thiazol-2-yl)quinolin-8-ol, the compound of Formula 1 as a light green solid (yield: 75%).

The 2-(benzo[d]thiazol-2-yl)quinolin-8-ol is an 8-hydroxyquinoline compound represented by Formula 1 and has a melting point of 189° C. to 191° C. As can be seen from FIG. 1, the NMR result and elemental analysis result of the compound are as follows:

$^1$H NMR (CDCl$_3$, 300 MHz) δ 8.51 (d, J=8.7 Hz, 1H), 8.32 (d, J=8.7 Hz, 1H), 8.16 (d, J=8.1 Hz, 1H), 8.05 (s, 1H), 7.99 (d, J=8.1 Hz, 1H), 7.54-7.24 (m, 4H), 7.24 (d, J=7.5 Hz, 1H); $^{13}$C NMR (75 MHz, CDCl$_3$) δ152.5, 137.5, 129.5, 129.3, 126.7, 126.3, 124.1, 119.3, 118.3, 111.2; HRMS (EI); m/z calcd for C$_{16}$H$_{10}$N$_2$OS 278.0514. Found 278.0478.

Example 1

Synthesis of 2-(2-(benzo[d]thiazol-2-yl)quinolin-8-yloxy)-N,N-diethylacetamide The N,N-diethylacetamide prepared in Synthesis Example (278 mg, 1 mmol), potassium carbonate (K$_2$CO$_3$, 276 mg, 2 mmol) and potassium iodide (KI, 17 mg, 1.5 mmol) were stirred in tetrahydrofuran with blown nitrogen to prevent oxidation which is caused by oxygen in air. Then, 2-chloro-N,N-diethylacetamide (225 mg, 1.5 mmol) was added to the mixture. The resulting mixture was stirred at 80° C. for 26 hours and extracted with dichrolomethane and distilled water. The obtained extracts were dried and purified by column chromatography (hexane:ethyl acetate=1:1, v/v) to yield a yellow solid of the compound 2 (yield: 63%).

Figure 2A:
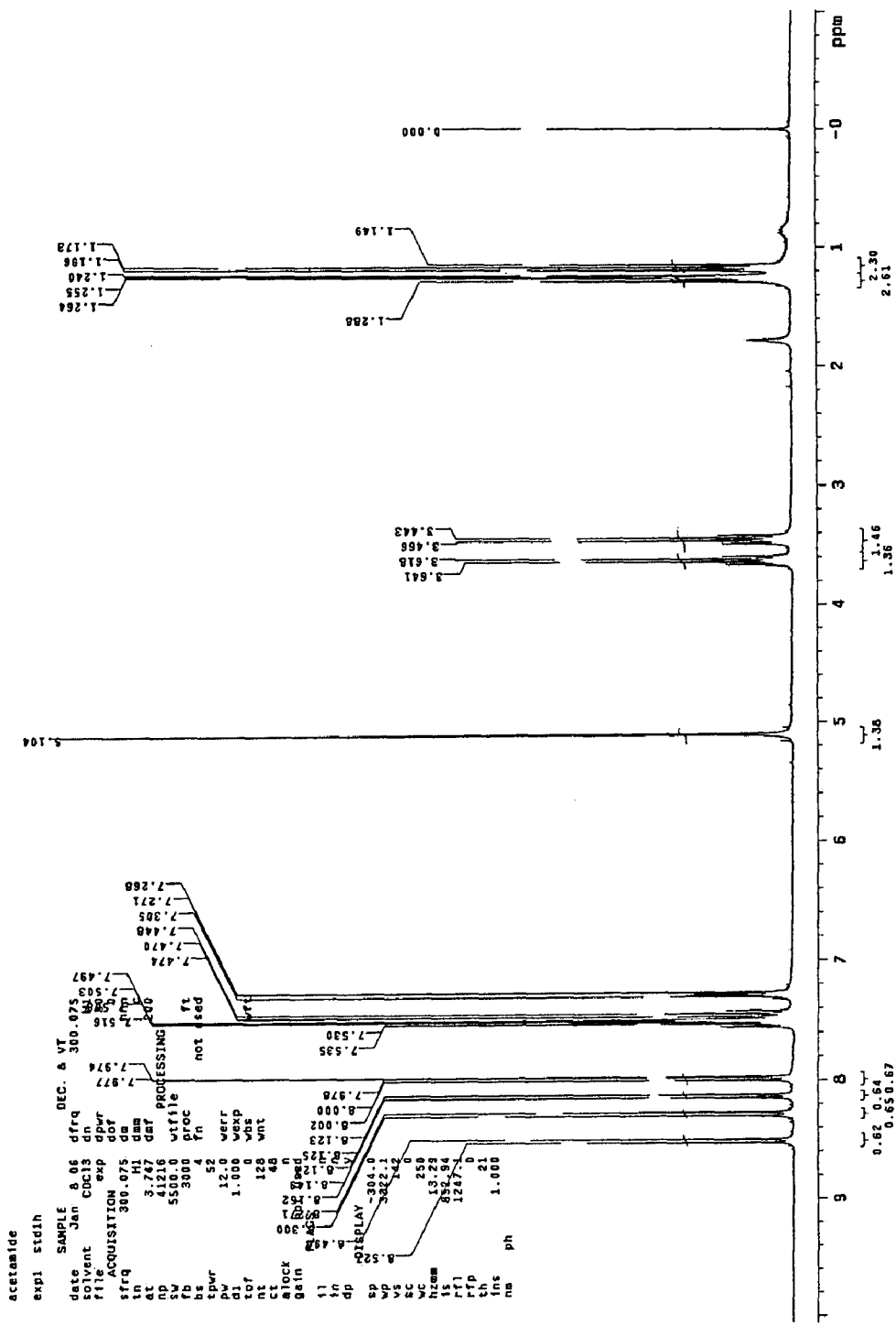
FIGS. 2a and 2b are a $^1$H-NMR spectrum and a $^{13}$C-NMR spectrum of an 8-hydroxyquinoline acetamide compound represented by Formula 2 according to the present invention, respectively.
Figure 2B:
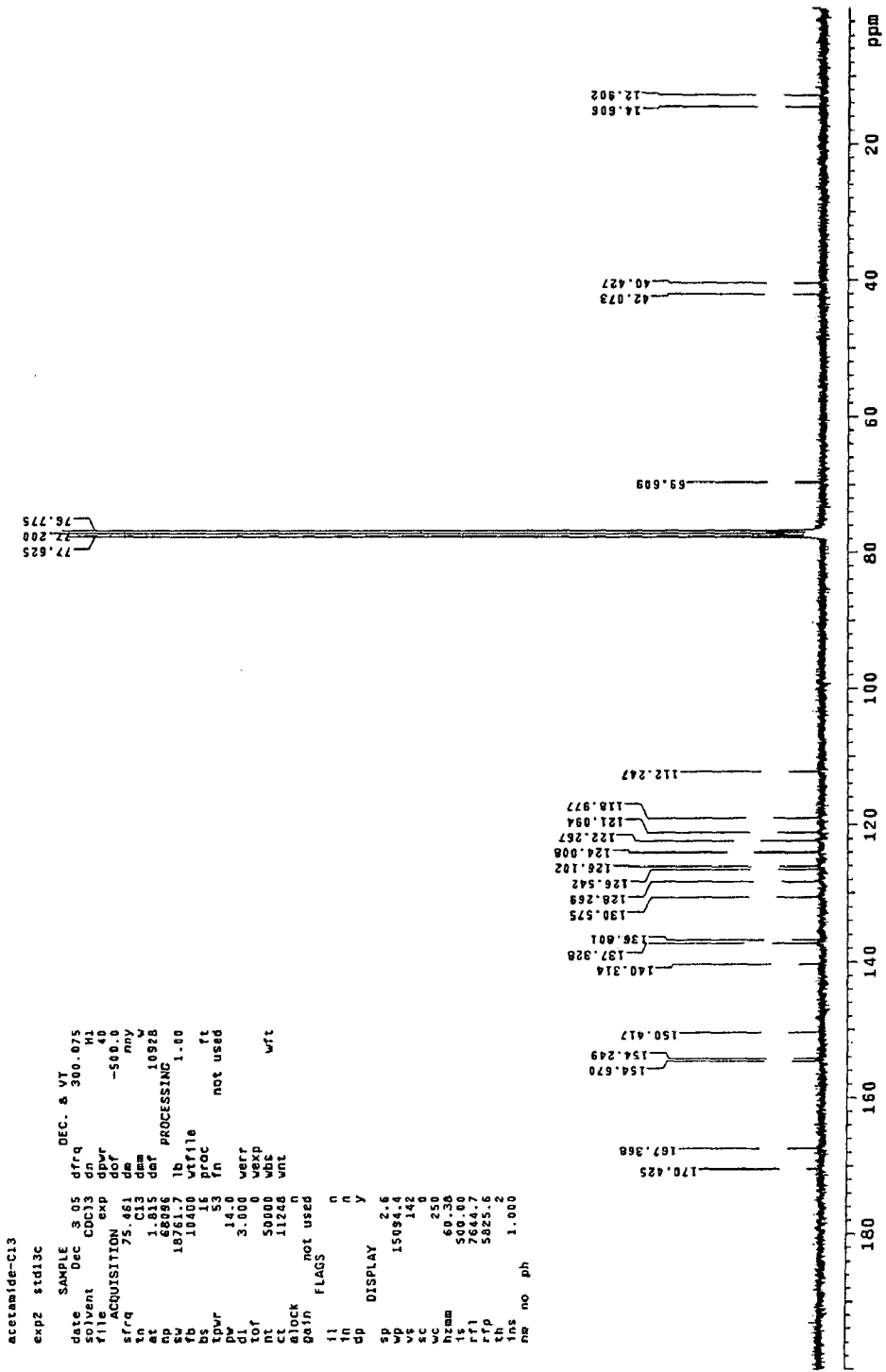

As can be seen from FIGS. 2a and 2b, the NMR result and elemental analysis result of the compound 2 are as follows:

$^1$H NMR (CDCl$_3$, 300 MHz) 8.51 (d, J=14.5 Hz, 1H), 8.29 (d, J=14.5 Hz, 1H), 8.14 (dd, J=11 Hz and 1.5 Hz, 1H), 7.99 (dd, J=11 and 1.5 Hz, 1H), 7.54-7.45 (m, 4H), 7.3-7.28 (m, 1H), 5.10 (s, 2H), 3.63 (q, J=11.5 Hz, 2H), 3.45 (q, J=11.5 Hz, 2H), 1.25 (t, J=12 Hz, 3H), 1.18 (t, J=11.7 Hz, 3H). $^{13}$C NMR (CDCl$_3$, 75 MHz) 170.4, 167.4, 154.7, 154.2, 150.4, 140.3, 137.3, 136.8, 130.6, 128.3, 126.5, 126.1, 124.0, 122.3, 121.1, 119.0, 112.4, 69.6, 42.1, 40.4, 14.6, 12.9. HRMS (EI) Calcd for C$_{22}$H$_{21}$N$_3$O$_2$S, 391.1354. Found 391.1356.

As a result, the compound 2 is confirmed to be 2-(2-(benzo[d]thiazol-2-yl)quinoline-8-yloxy)-N,N-diethylacetamide as one of compounds that can be represented by Formula 2.

Example 2

Synthesis of 2-(2-benzo[d]thiazol-2-yl)quinolin-8-yloxy)-N,N-diethylethanethioamide The 2-(2-(benzo[d]thiazol-2-yl)quinoline-8-yloxy)-N,N-diethylacetamide prepared in Example 1 (196 mg, 0.5 mmol) was dissolved in dry toluene. To the solution was added Lawesson's reagent (203 mg, 0.5 mmol). Then, the mixture was heated at 100° C. for 36 hours and allowed to cool to obtain a solid. The solid was purified by column chromatography (hexane:ethyl acetate=3.5:1, v/v) to yield a white solid of the compound 3 (yield: 62%).

Figure 3A:
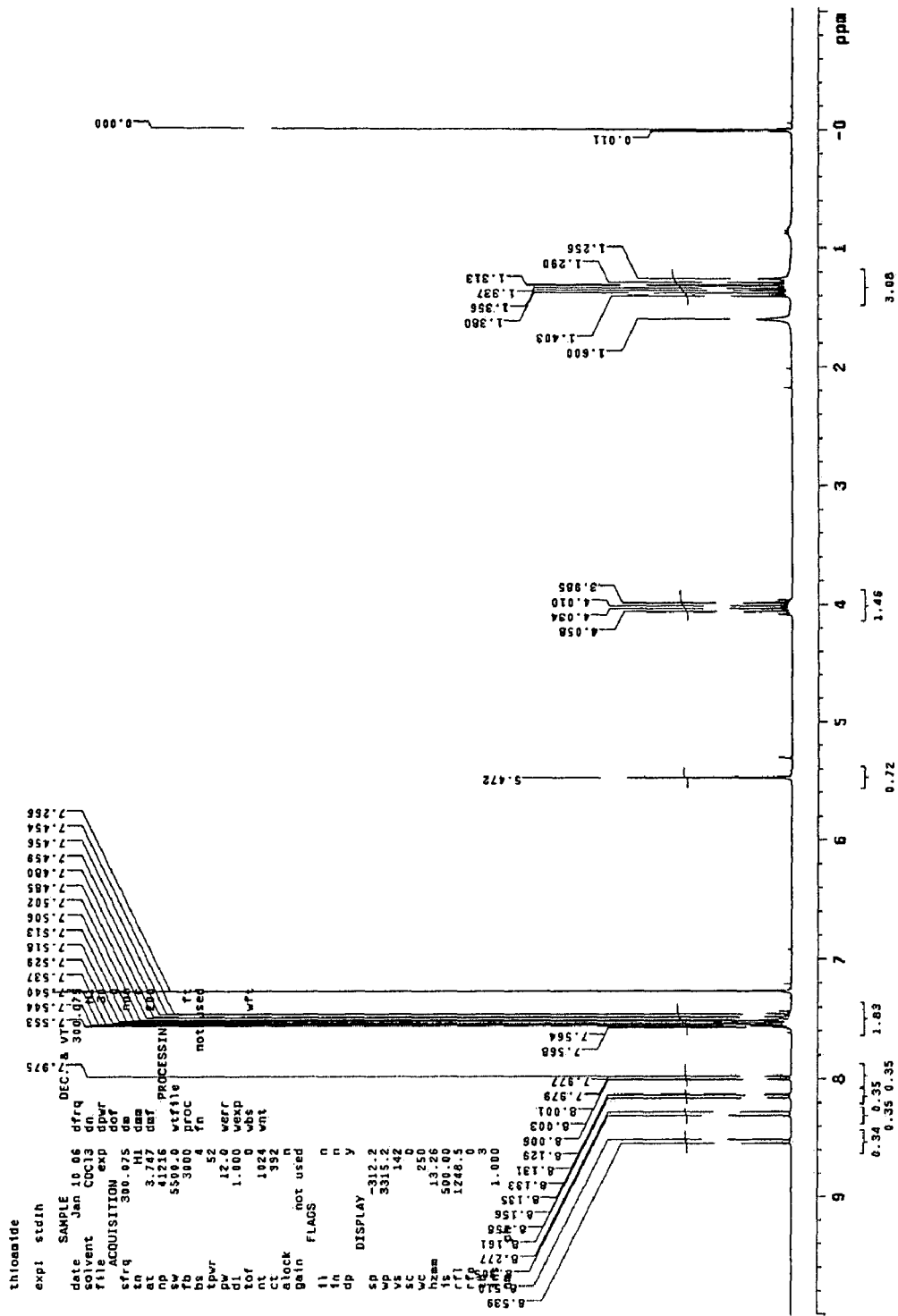
FIGS. 3a and 3b are a $^1$H-NMR spectrum and a $^{13}$C-NMR spectrum of an 8-hydroxyquinoline thioamide compound represented by Formula 3 according to the present invention, respectively.
Figure 3B:
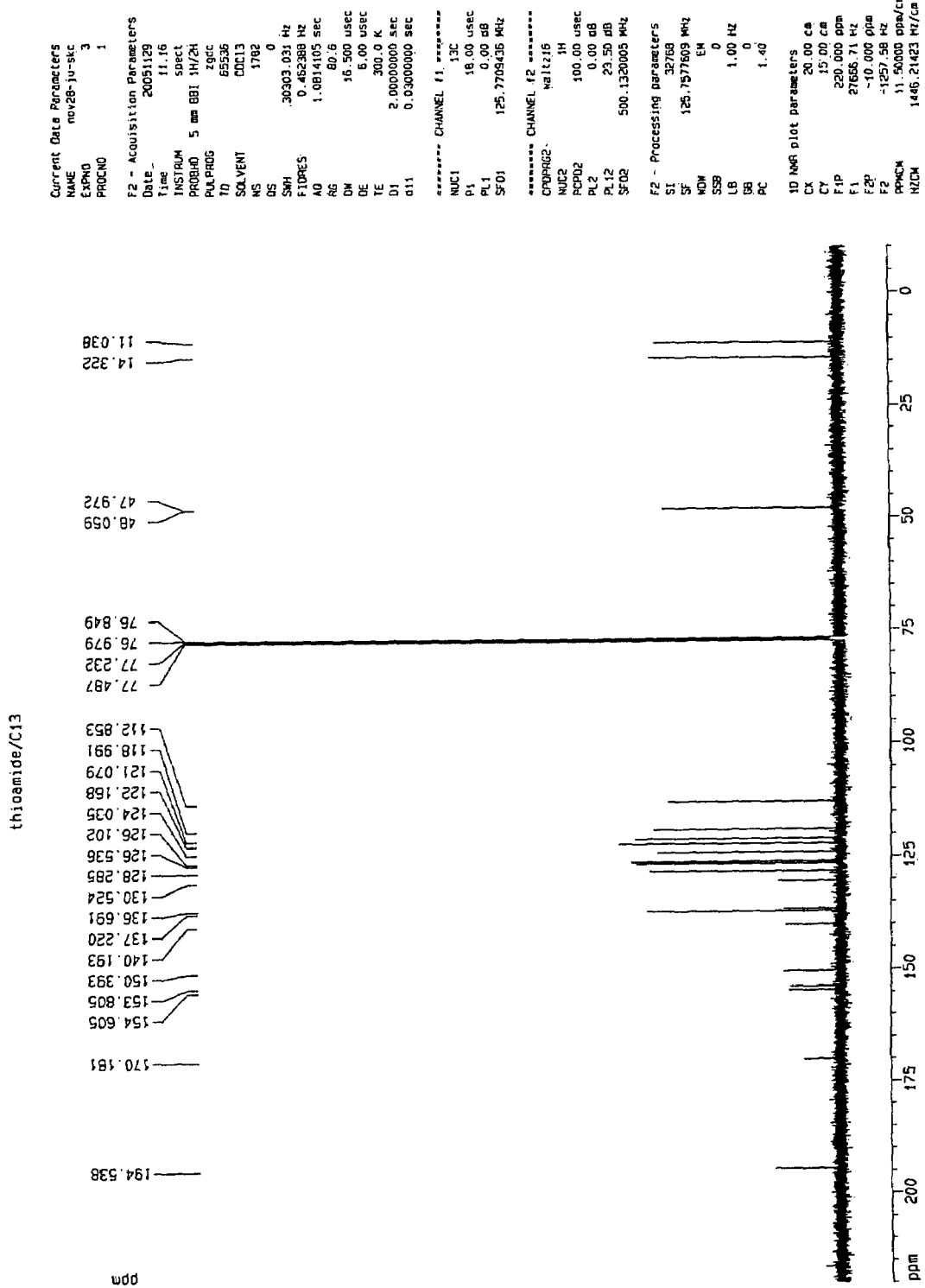

As can be seen from FIGS. 3a and 3b, the NMR result and elemental analysis result of the compound 3 are as follows:

$^1$H NMR (CDCl$_3$, 300 MHz) 8.52 (d, J=14.5 Hz, 1H), 8.29 (d, J=14 Hz, 1H), 8.14 (d, J=11.5 and 1 Hz, 1H), 7.99 (dd, =1 and 12 Hz, 1H), 7.57-7.45 (m, 5H), 5.47 (s, 2H), 4.05 (q, J=12 Hz, 2H), 4.00 (q, J=12.5 Hz, 2H), 1.38 (t, J=11.7 Hz, 3H), 1.31 (t, J=11.8 Hz, 3H). $^{13}$C NMR (CDCl$_3$, 125 MHz) 194.5, 170.2, 154.6, 153.8, 150.4, 140.2, 137.2, 136.7, 130.5, 128.3, 126.5, 126.1, 124.0, 122.2, 121.1, 119.0, 112.9, 76.8, 48.1, 48.0, 14.3, 11.0. HRMS (EI) Calcd for C$_{22}$H$_{21}$N$_3$OS$_2$, 407.1126. Found 407.1125.

As a result, the compound 3 is confirmed to be 2-(2-benzo[d]thiazol-2-yl)quinolin-8-yloxy)-N,N-diethylethanethioamide as one of compounds that can be represented by Formula 3.

Experimental Example 1

Test of Fluorescent Properties

The ionophoric properties of the 2-(2-(benzo[d]thiazol-2-yl)quinoline-8-yloxy)-N,N-diethylthioamide compound prepared in Example 2 were evaluated by fluorescence spectroscopy. Specifically, it could be confirmed from preliminary tests in accordance with various solvent conditions that the compound's behavior was optimized under an aqueous acetonitrile solution and a Tris buffer solution (pH=8.1) for the detection of metal ions in a biological reagent. Accordingly, tests herein were carried out under these conditions.

Figure 4:
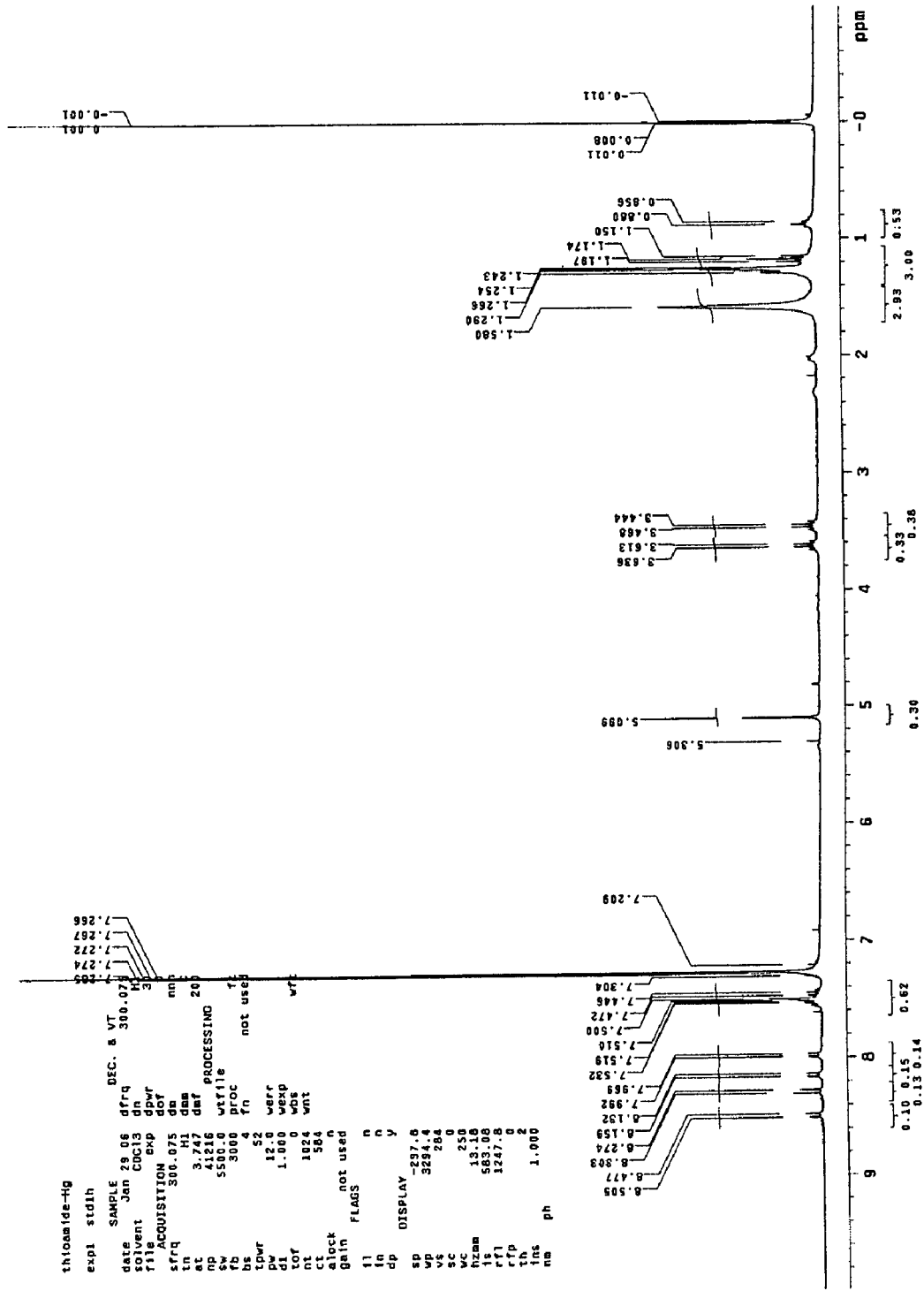
FIG. 4 is a $^1$H-NMR spectral graph illustrating conversion of an 8-hydroxyquinoline thioamide compound of Formula 3 into an 8-hydroxyquinoline acetamide compound of Formula 2, which results from desulfurization by addition of mercury ions according to the present invention.

The 2-(2-(benzo[d]thiazol-2-yl)quinoline-8-yloxy)-N,N-diethylthioamide compound exhibited a maximum adsorption band at 345 nm, and a very weak fluorescence at about 475 nm in an aqueous acetonitrile solution (excitation=345 nm, acetonitrile:water=30:70, v/v). Meanwhile, it could be seen from FIG. 4 that when the compound (represented by Formula 3, $5.0 \times 10^{-4}$ M) is reacted with a 100-fold concentration of metal perchlorate (where the metal is selected from: transition metals including Ni$^{2+}$, Cu$^{2+}$, Zn$^{2+}$, Cd$^{2+}$ and Hg$^{2+}$; alkali metals including Na$^+$ and K$^+$; and alkaline earth metals including Mg$^{2+}$ and Ca$^{2+}$), significant fluorescence enhancement for Hg$^{2+}$ only was observed.

Since the detection sensitivity of the 2-(2-(benzo[d]thiazol-2-yl)quinoline-8-yloxy)-N,N-diethylthioamide compound for mercury was considerably excellent, even the use of one-fold concentration of Hg$^{2+}$ leaded to a 167-fold increase in fluorescence intensity at 479 nm, as compared to the case where there is no mercury ion. The use of Cd$^{2+}$ only among these metal ions caused a 3.8-fold increase in fluorescence intensity, and other metal ions caused a slight increase (i.e. 2-fold or less) in fluorescence intensity.

In addition, the signaling property of the 2-(2-(benzo[d]thiazol-2-yl)quinoline-8-yloxy)-N,N-diethylthioamide compound was evaluated by fluorescence titration. While one-fold of mercury ions was added, as mercury ions increased, fluorescence intensity increased. However, when one or more-fold of mercury ions was added, an increase in fluorescence intensity was not observed any more. As a result of the fluorescence titration, the detection limit of the 2-(2-(benzo[d]thiazol-2-yl)quinoline-8-yloxy)-N,N-diethylthioamide compound was obtained from a graph showing a variation in fluorescence intensity as a function of a mercury ion concentration. The compound could be used to detect a micromole concentration of mercury ions in a chemical or biological system as $5.4 \times 10^{-7}$ M under a 30% aqueous acetonitrile solution (See FIG. 6).

Meanwhile, it is considered that mercury ion-selective fluorescence enhancement of the 2-(2-(benzo[d]thiazol-2-yl)quinoline-8-yloxy)-N,N-diethylthioamide compound is based on conversion of a thioamide group in the compound 3 into an amide group, as depicted in the following Reaction Scheme 3:

Reaction Scheme 3

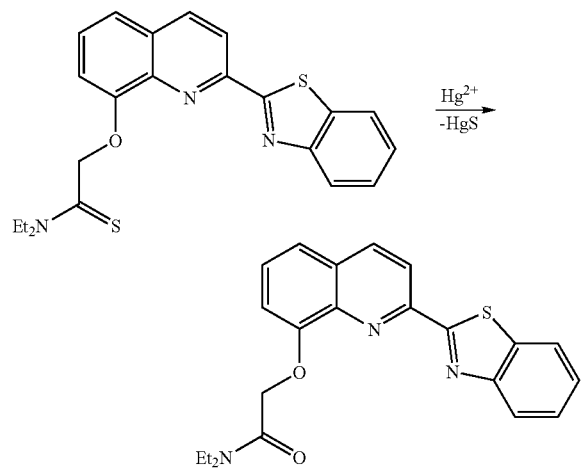

The conversion of the compound 3 into the compound 2, shown in Reaction Scheme 3, induced strong fluorescence emission. This phenomenon was confirmed from the results of EDTA experiments, NMR spectrum and Mass spectrum.

More specifically, the addition of 100-fold concentration of mercury ions to the compound 3 leaded to great fluorescence enhancement. Then, the addition of 1.000-fold concentration of EDTA to the mixture caused no further variation. On the other hand, when a 100-fold concentration of mercury ions was put in a system where the compound 3 and EDTA coexist, EDTA having strongly chelating capability effectively sequestered the mercury ions from interaction with the compound 3. For this reason, there was no variation in fluorescence intensity, which is caused by desulfurization (See FIG. 7).

Then, the compound 3 was reacted with five-fold concentration of mercury ions in a 30% aqueous acetonitrile solution to obtain a product. As apparent from FIG. 4, the product was confirmed to be the compound 2. In addition, it could be confirmed from mass spectrum that m/z of the compound 3 was 391.1. Based on the fore-mentioned results, chemical conversion of the compound 3 into the compound 2 by mercury ions was confirmed.

Figure 5:
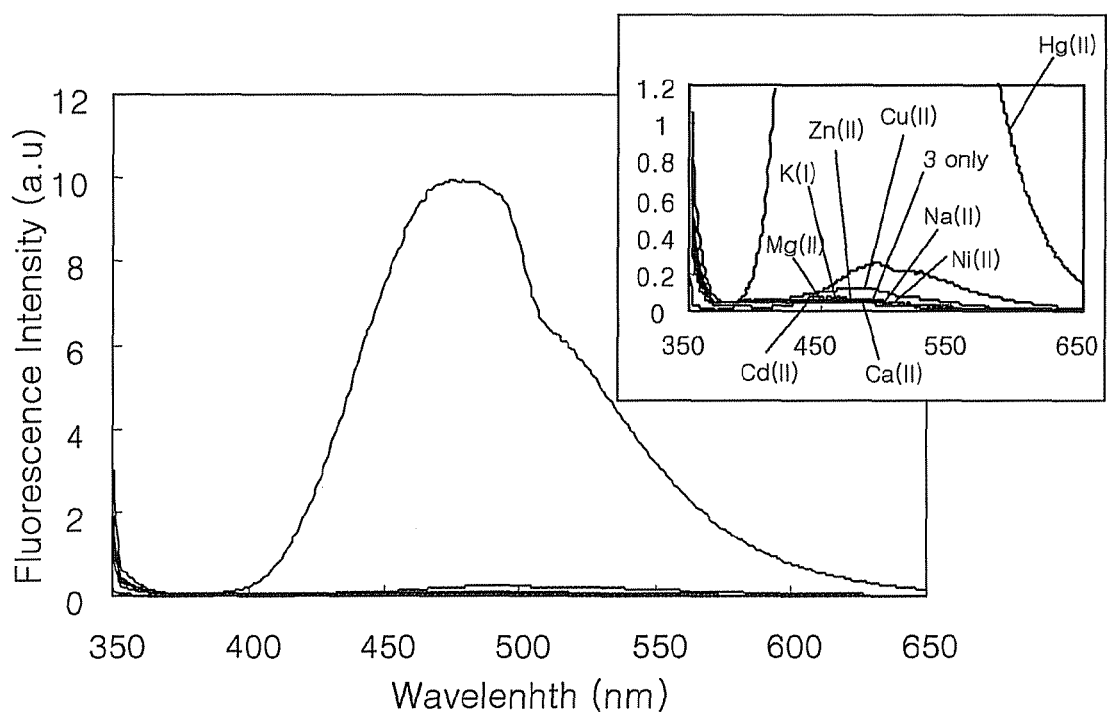
FIG. 5 is a fluorescence spectrum illustrating an 8-hydroxyquinoline thioamide compound of Formula 3 of the present invention according to the type of metal ions.

To confirm whether the compound of the present invention can be used under practical conditions for detection of mercury ions, sensitivity of the compound for mercury ions were evaluated in a system containing a large amount of physiologically important metal ions ($[Na^+]$=138 mM, $[K^+]$=4 mM, $[Mg^{2+}]$=1 mM, $[Ca^{2+}]$=3 mM, $[Zn^{2+}]$=0.02 mM, and $[Cu^{2+}]$=0.015 mM). As a result, it can be seen from FIGS. 5 and 8 that the compound was hardly affected by a large amount of other metal ions, when taking into consideration the sensitivity and detection limit.

Meanwhile, the 8-hydroxyquinoline thioamide compound of Formula 3 was dissolved in a mixed solvent of water and methanol, and a mixed solvent of water and dioxane, respectively, instead of water, acetonitrile or a mixture thereof, and the detection test of the solution for various metal ions was carried out by fluorescence spectroscopy. The result was shown in FIGS. 9a to 10b. Accordingly, to selectively detect mercury ions only, as a solvent to dissolve the 8-hydroxyquinoline thioamide compound, most preferred is to use of water, acetonitrile or a mixture thereof.

As apparent from the foregoing, by introduction of benzo[d]thiazol and N,N-diethylethanethioamide moieties serving as both a signaling site and an additional binding site into 8-hydroxyquinoline as a well-known binding site, the 8-hydroxyquinoline thioamide compound of Formula 3 according to the present invention can exhibit specificity for mercury ions only. Accordingly, the compound can be used as a mercury ion-selective chemodosimeter.

In addition, the compound of Formula 3 of the present invention has advantages in that it can exhibit considerably effective fluorescence specificity of an off-on type, detect a micromole of mercury ions from chemical and biological aqueous systems, and allow 100% desulfurization within 5 minutes, thus being considerably useful in the chemical industry.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An 8-hydroxyquinoline acetamide compound represented by Formula 2 below:

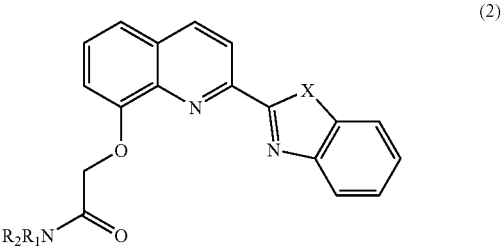

(2)

wherein X is S, O or NH; and $R_1$ and $R_2$ are each independently $C_{1-4}$ linear or branched alkyl.

2. The 8-hydroxyquinoline acetamide compound according to claim 1, wherein the compound of Formula 2 is 2-(2-(benzo[d]thiazol-2-yl)quinoline-8-yloxy)-N,N-diethylacetamide, 2-(2-(benzo[d]thiazol-2-yl)quinoline-8-yloxy)-N,N-dimethylacetamide, 2-(2-(benzo[d]thiazol-2-yl)quinoline-8-yloxy)-N,N-dipropylacetamide, or 2-(2-(benzo[d]thiazol-2-yl)quinoline-8-yloxy)-N,N-dibutylacetamide.

3. An 8-hydroxyquinoline thioamide compound represented by Formula 3 below:

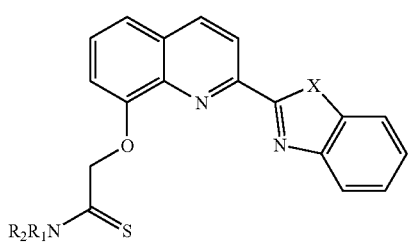

wherein X is S, O or NH; and $R_1$ and $R_2$ are each independently $C_{1-4}$ linear or branched alkyl.

4. The 8-hydroxyquinoline thioamide compound according to claim 3, wherein the compound of Formula 3 is 2-(2-(benzo[d]thiazol-2-yl)quinoline-8-yloxy)-N,N-diethylethanethioamide, 2-(2-(benzo[d]thiazol-2-yl)quinoline-8-yloxy)-N,N-dimethylethanethioamide, 2-(2-(benzo[d]thiazol-2-yl)quinoline-8-yloxy)-N,N-dipropylethanethioamide, or 2-(2-(benzo[d]thiazol-2-yl)quinoline-8-yloxy)-N,N-dibutylethanethioamide.

5. A method for preparing an 8-hydroxyquinoline acetamide compound by reacting an 8-hydroxyquinoline compound represented by the following Formula 1 with 2-chloro-N,N-diethylacetamide, potassium carbonate and potassium iodide in an organic solvent under an inlet gas atmosphere:

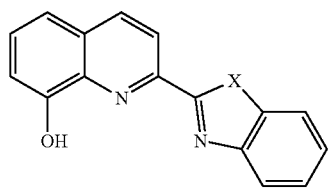

wherein X is S, O or NH.

6. The method according to claim 5, wherein the molar ratio of the 8-hydroxyquinoline compound of Formula 1, 2-chloro-N,N-diethylacetamide, potassium carbonate and potassium iodide is 1:1.2-2.0:1.0-2.0:0.05-0.2.

7. The method according to claim 5, wherein the organic solvent is tetrahydrofuran (THF).

8. A method for preparing a 8-hydroxyquinoline thioamide compound represented of Formula 3 below:

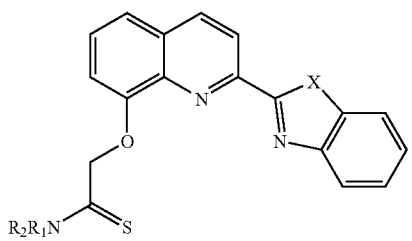

wherein X is S, O or NH; and $R_1$ and $R_2$ are each independently $C_{1-4}$ linear or branched alkyl, by reacting a 8-hydroxyquinoline acetamide compound of Formula 2 below:

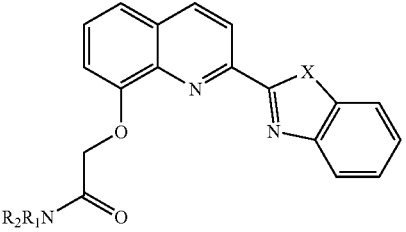

wherein X is S, O or NH; and $R_1$ and $R_2$ are each independently $C_{1-4}$ linear or branched alkyl, with a Lawesson's reagent in an organic solvent.

9. The method for preparing an 8-hydroxyquinoline thioamide compound according to claim 8, wherein the molar ratio of the 8-hydroxyquinoline acetamide compound to the Lawesson's reagent is 1:1.0-1.5 and the organic solvent is toluene.

10. A method for synthesizing an 8-hydroxyquinoline thioamide compound with selectivity for mercury ions as depicted in the following Reaction Scheme 1, the method comprising:

1) reacting an 8-hydroxyquinoline compound 1 represented by the following Formula 1 with 2-chloro-N,N-diethylacetamide, potassium carbonate and potassium iodide in an organic solvent under an inlet gas atmosphere to prepare an 8-hydroxyquinoline acetamide compound represented by Formula 2; and 2) reacting the 8-hydroxyquinoline acetamide compound with Lawesson's reagent in an organic solvent to prepare an 8-hydroxyquinoline thioamide compound represented by the following Formula 3;

Reaction Scheme 1

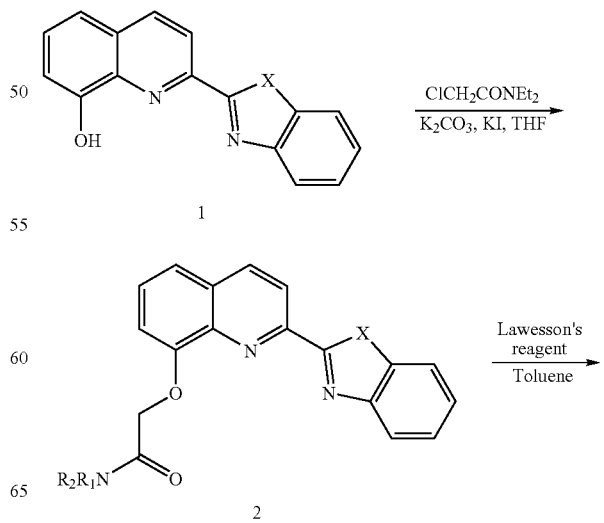

-continued

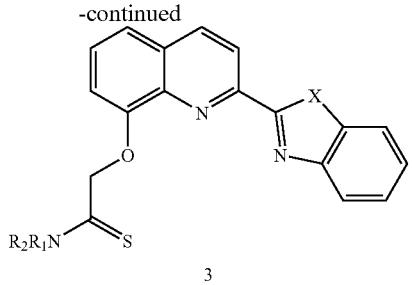

3 wherein X is S, O or NH; and $R_1$ and $R_2$ are each independently $C_{1-4}$ linear or branched alkyl.

11. A chemodosimeter for mercury ion-selective detection, the chemodosimeter comprising the 8-hydroxyquinoline thioamide compound according to claim 3.

12. A method for selectively detecting mercury ions, the method comprising:
dissolving the 8-hydroxyquinoline thioamide compound according to claim 3 in water, acetonitrile, or a mixed solvent of water and acetonitrile;
adding a desired reagent to the solution;
and detecting mercury ions by analyzing a fluorescence spectrum involved in desulfurization of mercury ions contained in the reagent with the 8-hydroxyquinoline thioamide compound, as depicted in the following Reaction Scheme 2:

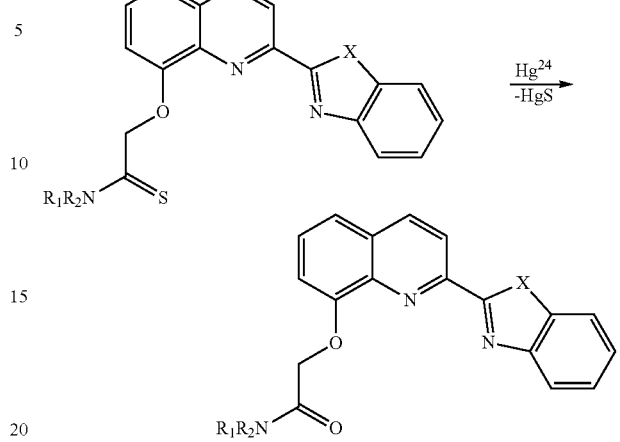

Reaction Scheme 2 wherein X is S, O or NH; and $R_1$ and $R_2$ are each independently $C_{1-4}$ linear or branched alkyl.

13. The method according to claim 12, wherein the mixed ratio of water and acetonitrile are 1:99-99:1.

14. The method according to claim 12, wherein the minimum detectable concentration of mercury ions is $5.4 \times 10^{-7}$ M.

* * * * *